United States Patent [19]

Angeletti et al.

[11] Patent Number: 4,894,471

[45] Date of Patent: Jan. 16, 1990

[54] CONTINUOUS PROCESS FOR THE ALKYLATION OF CH-ACID COMPOUNDS WITH ALKYL CARBONATES IN GAS-LIQUID PHASE TRANSFER CATALYSIS-CONDITIONS

[75] Inventors: Enrico Angeletti; Franco Trotta; Pietro Tundo; Paolo Venturello, all of Turin, Italy

[73] Assignee: Consiglio Nazionale Delle Richerche, Rome, Italy

[21] Appl. No.: 31,598

[22] Filed: Mar. 30, 1987

[30] Foreign Application Priority Data

Apr. 3, 1986 [IT] Italy .............................. 19971 A/86

[51] Int. Cl.$^4$ .................. C07C 121/66; C07C 121/68
[52] U.S. Cl. .................................... 558/378; 560/190; 560/203; 562/490; 562/492
[58] Field of Search ................ 558/369, 378; 560/190, 560/203; 562/490, 492

[56] References Cited

U.S. PATENT DOCUMENTS 4,012,428  3/1977  Ohno et al. ......................... 558/369

Primary Examiner—Joseph Paul Brust
Attorney, Agent, or Firm—Walter H. Schneider

[57] ABSTRACT

A continuous process for the alkylation of CH-acid compounds with dialkyl carbonates in gas-liquid phase transfer catalysis conditions is described, consisting of contacting a mixture of a CH-acid compound (arylacetonitrile or malonic diester) and of a dialkylcarbonate, optionally added with an inert carrier (constituted by a polar or aprotic polar liquid or by a gas), with a catalytic bed comprising alumina spheres carrying a base and a phase transfer catalyst.

8 Claims, No Drawings

CONTINUOUS PROCESS FOR THE ALKYLATION OF CH-ACID COMPOUNDS WITH ALKYL CARBONATES IN GAS-LIQUID PHASE TRANSFER CATALYSIS-CONDITIONS

The invention concerns a continuous process for the alkylation of CH-acid compounds.

More particularly, the invention concerns a continuous process for the alkylation of CH-acid compounds with alkyl carbonates in gas-liquid phase transfer catalysis conditions.

The alkylation of CH-acid compounds is a reaction widely used because it allows to obtain a large variety of interesting compounds starting from a large number of methine or methylene compounds, which are activated by the presence of Z and Z' substituents able to give rise to a negative charge by reaction with a base:

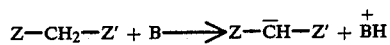

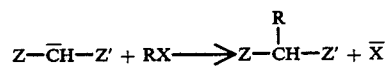

The case of a methylene compound is shown in reaction (1). The Z-CH-Z' anion may be obtained by reacting the CH-acid compound with a stronger base (alkoxydes, hydrides, hydroxides etc.). The synthetic methods for carrying out said reactions comprise reactions in "classic" conditions (the anion is first generated by reaction with a stronger base and the alkyl halide is then added; see for instance H. O. House, "Modern Synthetic Reactions", IX (ed. Benjamin, New York 1972)), solid-liquid phase transfer catalysis (SL-PTC) or liquid-liquid (LL-PTC) reactions (contemporaneous presence of the base, of the CH-acid compound and of the alkylating agent; see M. Makosza, J. Org. Chem. 43, 4682 (1978)).

Recently, the reaction has been carried out also in gas-liquid phase transfer catalysis conditions (GL-PTC) (see E. Angeletti, P. Tundo and P. Venturello, Italian patent application No. 23699 A/82). In the latter technique the catalyst, immobilized on an inorganic carrier, is in the liquid state in the reaction conditions. The reagents mixture is fed, through a pump, to the column where the catalytic bed is placed, and is converted to the vapor phase. The products are collected by condensation at the column output.

In all the previously reported synthesis reactions, the base used in the reaction is progressively consumed and it is then used in at least stoichiometric amounts, according to the equations (1) and (2).

A first drawback common to all these processes is therefore provided by the high base consumption, particularly serious in the case of relatively expensive bases (hydrides, alkoxides); whereas a much more relevant drawback is to be found in the low selectivity of the processes themselves, yielding sometimes mixtures of monoalkylderivatives and of dialkylderivatives in very similar amounts.

It has now been surprisingly found that the reaction between CH-acid compounds and dialkylcarbonates in GL-PTC conditions cannot run only for an indefinite time with catalytic amounts of base, but it is also highly selective to the monalkylation product. The use of dimethylcarbonate (DMC) as a low cost reagent, produced industrially and non-toxic and innoxious as other methylating agents such as dimethylsulfate and methyliodide, proved to be particularly interesting. On the other hand, just the selective monomethylation of CH-acid compounds is often desired for the preparation of products endowed with high practical importance, as it will be hereinafter apparent.

The process according to the invention may be summarized in the following scheme (3):

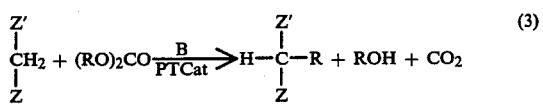

wherein at least one of Z and Z' is, as already shown in schemes (1) and (2), an electron-attractive group; B is a base; PTCat is a phase transfer catalyst and generally an anionic activator; R is a $C_1$–$C_4$ lower alkyl, preferably methyl, ethyl or n-propyl, and more preferably methyl. The above reported scheme has been particularly carried out on arylacetonitriles and malonic esters.

According to equation (3), the reaction may run indefinitely because the acidity is removed from the reaction medium in form of $CO_2$. In fact, some reactions were carried out for many days without loss of catalytic activity of the solid bed. The latter is prepared by dissolving the desired amount of base catalyst in water and adding to the solution small spheres of inert material as solid carrier. Water is then removed by distillation under vacuum and the spheres so impregnated are placed in an oven at 130° C. overnight.

As a base, alkali or alkali-earth metal carbonates, bicarbonates or hydroxides may be used; in practice, carbonates are preferably used, and particularly $K_2CO_3$.

The phase transfer catalysts, to be used in the process of the invention, belong to the most various classes. They are generally high molecular weight compounds, liquid at the reaction temperature and giving for instance an activation to the anion to be reacted.

Polyalkyleneglycols, having a molecular weight ranging from about 600 to about 40.000 may be used; moreover, so called "Nixolens", i.e. condensation products of ethylene oxide and propylene oxide, commercially available under the trade-marks Nixolen NS, Nixolen VS and Nixolen SL, polyamides and copolyamides having polar character may also be used.

As an inert material to be used as a carrier, in form of small spheres or other particles, alumina of different kinds can be used, particularly corundum, i.e. highly sinterized α-alumina. When small spheres are used, they preferably have a diameter ranging from 0.05 to 5 mm, preferably from 1/16 inch (1.6 mm) to ¼ inch (6.4 mm).

The weight ratio base: inert carrier and PTCat: inert carrier, may vary within wide limits. For instance, from 1 g to 30 g of $K_2CO_3$ per 100 g of corundum spheres may be used, and from 0 g to 20 g of polyethyleneglycol always for 100 g of a carrier.

The reaction temperatures are usually comprised between 120° and 250° C., also according to the process pressure, which may range from 0.01 to 5 bar according to the CH-acid used but which usually ranges from about 20 millibar to the normal pressure.

The CH-acid compounds may be subjected to the reaction either as such or carried by gas or vapours acting as carrier. Sometimes the carrier is the dialkylcarbonate itself, used in excess; in other cases the use of tetrahydrofuran, or cyclohexane, or similar apolar or aprotic polar compounds, inert in the reaction conditions, or also of nitrogen or carbon dioxide, is useful.

The molar ratio between the CH-acid compound and dialkylcarbonate may vary from 1:1 to 1:60. The flow rate of the mixture through the catalytic bed (factor of high relevance for the conversion yields) depends on the temperature, pressure, and obviously on the amount of catalytic bed. Flow rates ranging from 5 to 50 ml/hour of liquid mixture, per 100 g of catalytic bed proved to be generally suited.

The following examples (with the exclusion of Example 8) were carried out in glass columns (inner diameter about 15 mm, effective height about 5–50 cm) containing 5–100 g of corundum spheres having 0.4 mm in diameter impregnated, in the above described way, with an aqueous solution containing $K_2CO_3$ and PEG 6000 or PEG 35000 (polyethyleneglycols, average molecular weight 6000 and respectively 35000) in such an amount that the support contains about 5% by weight of both. The column was thermostatized by continuous circulation of oil; the reagent mixture and of the optional carrier was fed at the liquid state and turned into the gaseous state in the column itself. The products were collected by condensation at the column exit.

All the reactions were carried out by continuously feeding a liquid mixture of dialkylcarbonate and CH-acid compound (molar ratio 4:1) in the absence or presence of a solvent (cyclohexane or THF).

The temperature was, in any way, 180° C. and the reactions were almost always carried out at atmospheric pressure. The flow at which the reagents were fed into the column was, according to each case, of 5,8,10 and 20 ml/h. The constant activity of the catalytic bed has been assayed also by using again the solid bed in subsequent reactions.

The results reported hereinafter concern phenylacetonitrile (on which an higher number of reactivity tests has been carried out), p-isobutyl-phenylacetonitrile (intermediate for the synthesis of an important non-steroidal antiinflammatory drug: Ibuprofen), (6-methoxy-2-naphthyl)-acetonitrile (intermediate of Naproxen, another known antiinflammatory drug) and the dimethyl and diethyl esters of malonic acid.

The composition of the mixture collected at the column exit, because of chromatographic phenomena, is first variable; it is therefore necessary to await some hours for the reaction to reach regimen and the reaction products mixture to be constant.

The following examples do not limit the invention in any way.

EXAMPLE 1

Phenylacetonitrile and dimethylcarbonate (a) By passing a 1:4 mixture (in moles) of $PhCH_2CN$ and DMC on 95 g of carborundum carrying 5% by weight of $K_2CO_3$ and 5% by weight of PEG 6000, at a flow-rate of 8 ml/h, the composition of the products mixture was: $PhCH_2CN$ 0.8%, $PhCHCH_3CN$ 98.1%, $PhC(CH_3)_2CN$ 1.1%.

(b) On 80 g of the bed as in (a), with a flow-rate of 20 ml/h, after 8 hours, at the equilibrium, the following composition was observed: $PhCH_2CN$ 27.0%, $PhCHCH_3CN$ 73.0%, $PhC(CH_3)_2CN$ 0.0%.

(c) Operating under the same conditions of (b), but with a flow-rate of 16 ml/h, the following composition was obtained: $PhCH_2CN$ 12%, $PhCHCH_3CN$ 88.0%, $PhC(CH_3)_2CN$ 0.1%.

(d) Operating as in (b) and with the same recovered bed, at 10 ml/h, the following composition was obtained: $PhCH_2CN$ 2.0%, $PhCHCH_3CN$ 97.5%, $PhC(CH_3)_2CN$ 0.5%. The catalytic bed, after the second experience, was of brown color, probably for secondary polymerization reactions, but it weighed 82 g that is only 2 g more in comparison with the starting bed, although about 70 g of phenylacetonitrile had passed through the column.

(e) In order to show the high selectivity in the monoalkylation reaction, the same reaction mixture, obtained in (d), containing 97.5% of monomethylated product and moreover DMC for at least 3 molar equivalents, was passed on a bed of similar composition in the same reaction conditions, but with a flow-rate of only 5 ml/h. At the equilibrium the starting $PhCH_2CN$ was not obviously observed, but the dimethylderivative did not exceed 4.1%. From these data, di-alkylation appears to be markedly unfavoured.

(f) Operating under the same conditions as in (a), but with the bed containing only 5% $K_2CO_3$, the observed conversion in $PhCHCH_3CN$ was 46%.

(g) The high reactivity, completely unusual, of phenylacetonitrile in GL-PTC is demonstrated by the fact that, carrying out the reaction with the same reagents and under comparable conditions but in liquid phase, the reaction rate is dramatically low, as it can be deduced from the following experiment; a stirred solution of 30 g of PEG 6000, 3.0 g of anhydrous potassium carbonate, 1.1 ml (10 mmoles) of phenylacetonitrile and 8.4 ml (100 mmoles) of DMC was heated to 100° C. After 70 hours the reaction mixture showed only a 1% conversion.

EXAMPLE 2

Phenylacetonitrile and diethylcarbonate

The reaction was carried out using 95 g of a catalytic bed comprising corundum spheres carrying 5% by weight of $K_2CO_3$ and 5% by weight of PEG 6000. 60 Ml of cyclohexane as a gaseous carrier were added to the 1:4 mixture (in moles) of $PhCH_2CN$ and DEC (respectively 11.5 ml and 48.6 ml), because DEC is a higher-boiling compound than DMC. The flow-rate was 10 ml/h. At the equilibrium a conversion of 28% in monoethylated product and the total absence of the di-alkylation product was observed.

EXAMPLE 3

Phenylacetonitrile and di-n-propylcarbonate

This test was carried out under the same reaction conditions of phenylacetonitrile with DEC, but on a catalytic bed of only 45 g. The 1:4 mixture (in moles) of phenylacetonitrile and DPC (6.2 ml and 31 ml) was added with 40 ml of cyclohexane as a carrier. At the equilibrium the conversion in the monoalkylation product was 11%, with total absence, also in this case, of the di-alkylation product.

EXAMPLE 4 p-Isobutylphenylacetonitrile and dimethylcarbonate

Since this nitrile has a boiling point markedly higher than the reaction temperature and remains longer in the column, the process was carried out in the presence of solvent (THF) and with a smaller amount of bed. 45 g of catalytic bed having the same compositions of the previous ones were therefore placed in the column. The reaction mixture was prepared by mixing 14.5 ml of p-isobutylphenylacetonitrile with 25 ml of DMC (1:4 in moles). 72 ml of THF as carrier were added thereto.

Operating at a flow-rate of 10 ml/h, the products mixture exhibited an exclusive conversion in the monomethylated product (2-(4-isobutyl-phenyl)propionitrile) of 44.0%.

By passing again the previously collected products mixture, enriched in DMC in a quantity double than the one of the previous experience, on the same bed and under the same conditions, the conversion increased to 92% of the monomethylated product and the total absence of the double methylated product was observed. In order to optimize the conversions and relying on the fact that said nitrile appears to be even more selective than phenylacetonitrile in the monoalkylation, another test was carried out under the same reactions conditions, but using 15 molar equivalents of DMC. At the equilibrium, the conversion in the monomethylated compound was 95.0%, the di-alkylation product being less than 0.4%.

EXAMPLE 5

(6-Methoxy-2-naphthyl)acetonitrile and dimethylcarbonate 3.0 g of 6-methoxy-2-naphtylacetonitrile were dissolved in 38 ml of DMC (30 molar equivalents) and 20 ml of THF; the solution was passed on 5.2 g of bed (same composition of Example 4) at atmospheric pressure, 180° and at a flow-rate of 10 ml/h. The collected reaction mixture showed a conversion of 60% in the monoalkylation product (2-(6-methoxy-2-naphtyl)propionitrile) and no trace of the di-alkylation product.

Operating in the same conditions with a 60 times molar excess of DMC and under vacuum (about 50 torr), the condensed product exhibited a 10% conversion in the sole mono-alkylation compound.

EXAMPLE 6

Dimethyl malonate and dimethylcarbonate (a) 80 g of corundum carrying 5% by weight of $K_2CO_3$ and 5% by weight of PEG 6000 were used. The mixture dimethyl malonate-dimethylcarbonate was 1:4 in moles; the flow-rate was 20 ml/h. 17.5% Conversion in the monoalkylation product was observed without any trace of the dialkylation compound.

(b) Increasing the bed amount to 95 g the conversion rose to 25% for the monomethylated product, always with total absence of the di-alkylation product.

(c) By operating as in (b), but with a bed constituted by 95 g of corundum carrying 5% by weight of $K_2CO_3$ and 10% by weight of PEG 6000, at a slower flow-rate (8 ml/h) the composition of the products mixture was: dimethyl malonate 28.0%, dimethyl 2-methylmalonate 67.0%, dimethyl 2.2-dimethyl malonate 5.0%.

EXAMPLE 7

Diethyl malonate and diethylcarbonate

In a similar way to phenylacetonitrile, DEC turns out to be less reactive than DMC. The reaction was carried out using 95 g of corundum carrying 5% by weight of $K_2CO_3$ and 5% by weight of PEG 6000. The flow-rate was kept at 10 ml/h, but 40 ml of cyclohexane as a carrier were added to the mixture diethyl malonate-diethylcarbonate (1:4 in moles, 15 ml : 49 ml). Only the monoethylated product was obtained with a conversion of 13%.

EXAMPLE 8 p-Isobutylphenylacetonitrile and dimethylcarbonate

The reaction was carried out in a stainless steel vertical column, 100 cm high and 5 cm in diameter, filled with a catalyst so prepared:

2000 g of corundum spheres ($Al_2O_3$ 90%; $SiO_2$ 8.3%; $Na_2O$ 0.04%; $TiO_2+Fe_2O_3$ 0.2%; $CaO+MgO$ 0.3%; $K_2O$ 0.5%), 1.5 mm in diameter, were added to the solution of 100 g of PEG 35000 and 100 g of anhydrous $K_2CO_3$ in 3000 ml of water. Water was then removed at 50° C. under reduced pressure and the spheres were dried at 130° C. in air-oven for 24 hours. Diathermic oil at 250° C. was circulated in the column jacket. A mixture—preheated at 60° C.—obtained from 2815 ml of p-isobutylphenylacetonitrile and 42185 ml of dimethylcarbonate (molar ratio 1:25), added with 50 g of $K_2CO_3$ as a dehydrating agent, was fed from the bottom. The feeding rate was 270 ml/hour for the whole test duration. At the same time, always from the bottom, a slight nitrogen flow was passed into the column.

After the first 5 hours, the system stabilized and the mixture at the column output exhibited (GLC analysis) a conversion to p-$(CH_3)_2CH-CH_2-C_6H_4-CH(CH_3)CN$ higher than 99%, with a yield higher than 95%. These data remained constant for the whole duration of the test (7 days).

The results obtained operating in GL-PTC conditions show that the reaction is catalytic, evolving $CO_2$ during the reaction course and that, surprisingly, the dialkylcarbonates do not act as carboxyalkylating agents, but only as methylating agents through an unusual mechanism, not yet investigated; in other words, neither Ar—CH(COOR)—CN nor $(COOR')_2$CHCOOR, which are main products when strong bases are used (see Indian Patent No. 141.315; C.A. 92, 128.585 (1980)), were not detected in the mixtures of the obtained products.

It should be noted that the alkylation of arylacetonitriles in LL-PTC conditions, although yielding the mo-noalkylation product, is not analogously selective: M. Sabbatini et al. (Boll. Chim. Farm. 117, 325–330 (1978)), working in LL-PTC conditions, obtained remarkably lower conversion and/or monoalkylate/dialkylate ratios: for instance, conversions 93%, ratio 3:1; conversion 74%, ratio 8.5:1, conversion 27%, ratio 12.5:1; according to the present invention a 92% conversion corresponds to the absence of dimethyl derivative.

Even operating in GL-PTC conditions, but using alkyl halides as alkylating agents, the reaction was not selective: by flowing 0.15 moles of $PhCH_2CN$ and 0.60 moles of $(CH_3)SO_4$ on 400 g of $K_2CO_3$ containing 5% by weight of PEG 6000, at 20 torr., 180° C. and with a flow-rate of 20 ml/h a product mixture is obtained containing: $PhCH_2CN$ 37.5%, PhCHCH CN 55% and PhC(CH )2CN 7.5%.

By using methyl iodide as alkylating agent, in similar conditions, a 45% conversion in monomethylderivative and 5% in di-alkyl derivative was obtained. It should be pointed out that, in similar conditions, the reaction bed is not actually catalytic because it is consumed when the reaction proceeds (the potassium carbonate is transformed into the corresponding sulfate or iodide).

Many of the most common and important non steroidal antiinflammatory agents belong to the class of phenylpropionic acids.

In addition to the already cited Ibuprofen and Naproxen, MK-830 (2-(3-chloro-4-cyclohexyl)-phenylpropionic acid), Fenoprofen (2-(3-phenoxy phenyl)propionic acid, Flurbiprofen (2-(3-fluoro-4-phenyl)-phenylpropionic acid) may also be cited.

We claim:

1. A continuous process for the monoalkylation of a CH-acid compound selected from (1) an arylacetonitrile in which the aryl is, 6-methoxy-2-naphthyl, phenyl, p-isobutylphenyl, 3-phenoxy-phenyl, 3-fluoro-4-phenyl-phenyl, and 3-chloro-4-cyclohexyl phenyl and (2) methyl or ethyl malonic acid diester, which comprises introducing a liquid mixture of said CH-acid compound and a $C_1$–$C_4$ dialkyl carbonate in a compound/carbonate molar ratio of 1:1–60 into a vapor phase reaction zone maintained at a temperature of 120°–250° C. and a pressure of 0.01–5 bar and containing a catalyst bed comprising (a) a base selected from an alkali or alkaline earth metal carbonate, bicarbonate or hydroxide, (b) a phase transfer catalyst selected from polyalkylene glycols and block or random copolyalkylene glycols, condensation products of ethylene oxide and propylene oxide, and polyamides and copolyamides, and (c) an inert catalyst support comprising alumina in particulate form; the flow of said liquid mixture into said reaction zone being at a rate of 5–50ml.hr of mixture per 100 g of catalyst bed; and recovering the monalkylated CH-acid product by condensing the resultant reaction products.

2. A process according to claim 1 in which the base is potassium carbonate.

3. A process according to claim 2 in which the phase transfer catalyst is polyethylene glycol having an average molecular weight of 6000–35000.

4. A process according to claim 3 in which the inert alumina carrier is in the form of corundum spheres of 1.6–6.4 mm average diameter.

5. A process according to claim 4 in which the catalyst support contains from 1–30 g of the base and 1–20 g of the phase transfer catalyst per 100 g of catalyst support.

6. A process according to claim 1 in which the reaction pressure is atmospheric.

7. A process according to claim 1 in which the mixture is conducted through the reaction zone by means of a carrier comprising an excess of the dialkyl carbonate or an inert gas.

8. A process according to claim 1 in which the CH-acid compound is selected from phenylacetonitrile, isobutylphenylacetonitrile, 6-methoxy-2-naphthylacetonitrile and dimethyl malonate and the alkylating agent is dimethyl carbonate.

* * * * *